United States Patent [19]

Schneider

[11] Patent Number: 4,986,815
[45] Date of Patent: Jan. 22, 1991

[54] NASOGASTRIC TUBE HOLDING DEVICE
[75] Inventor: Barry L. Schneider, Deerfield, Ill.
[73] Assignee: Hollister Incorporated, Libertyville, Ill.
[21] Appl. No.: 448,224
[22] Filed: Dec. 11, 1989
[51] Int. Cl.$^5$ ............................................. A61M 25/00
[52] U.S. Cl. .................................... 604/180; 604/178; 128/DIG. 26
[58] Field of Search ................. 604/77, 174, 177–180, 604/250; 254/28; 269/188, 202, 212, 214

[56] References Cited
U.S. PATENT DOCUMENTS

| | | | |
|---|---|---|---|
| 3,046,989 | 7/1962 | Hill | 604/180 |
| 3,760,811 | 9/1973 | Andrew | 128/DIG. 26 X |
| 4,120,304 | 10/1978 | Moor | 604/180 |
| 4,360,025 | 11/1982 | Edwards | 604/180 |
| 4,738,662 | 4/1988 | Kalt et al. | 604/180 |
| 4,804,374 | 2/1989 | Laskody | 604/180 |
| 4,932,943 | 6/1990 | Nowak | 604/180 |

Primary Examiner—C. Fred Rosenbaum
Assistant Examiner—Corrine Maglione
Attorney, Agent, or Firm—Tilton, Fallon, Lungmus

[57] ABSTRACT

A tube holding assembly particularly suitable for supporting a nasogastric feeding tube so that such a tube is not shifted accidentally out of position during use. The assembly includes a flexible nose pad adapted to be adhesively secured to a wearer's nose, a mounting pin projecting from a distal edge of the pad, and a pair of clamping jaws pivotally carried by the projecting end portion of the pin. The jaws have interdigitating tube-clamping plates disposed beneath the pin and a latching mechanism located in a readily viewable and accessible position above the pin.

10 Claims, 2 Drawing Sheets

NASOGASTRIC TUBE HOLDING DEVICE

This invention relates to the medical device field and, more specifically, to a device for immobilizing a nasogastric tube, such as a nasogastric feeding tube, in relation to a patient undergoing treatment.

BACKGROUND AND SUMMARY

Nasogastric tubes are available in a variety of sizes and materials, the selection for any given patient depending on factors such as the size and age of the patient, the expected duration of the intubation, and the precise purpose for such intubation. In general, nasogastric tubes are commonly available in sizes ranging between 6 to 18 French (2 to 6 millimeters) although even smaller sizes are known. Sizes of 8 to 12 French are often used for adult nasogastric feeding tubes whereas sizes of 5 French or smaller are sometimes used for infant feeding tubes. In contrast to tubes used for aspirating purposes, which are commonly formed of fairly stiff materials such as polyvinyl chloride for resisting collapse under suction, feeding tubes are usually formed of materials that are relatively soft or of low durometer readings such as, for example, silicone rubber.

Copending co-owned application 197,826, filed May 23, 1988, discloses a nasogastric tube holding device having a pair of clamping jaws that are readily adjustable for holding nasogastric tubes of different sizes and durometer values. The clamping jaws are pivotally mounted immediately adjacent the edge of a flexible pad that is adhesively secured over a wearer's nose when the device is in use. The jaws may be securely latched together and are maintained in such latched condition by positive action rather than spring action, but are nevertheless separable when adjustment or release of a nasogastric tube is required. Close proximity of the jaws to the end of the patient's nose, and the relative stiffness of that portion of the pad overlying the ridge of the nose, eliminates or greatly reduces any likelihood of pistoning actions sometimes found in prior art devices. In general, the nasogastric tube holder of the copending application has been found highly effective under a variety of conditions, overcoming the described shortcomings of the prior art, especially when the nasogastric tubes are used for aspiration.

When a nasogastric tube is used for feeding purposes, special problems may be presented. While the relative softness of a feeding tube enhances patient comfort and is desirable for other reasons as well, the ease with which such a tube may be deformed presents the problem of achieving an effective non-slipping clamping action without at the same time unacceptably deforming the tube. If only a gentle clamping force is applied, the holding action may be insufficient to withstand a strong or abrupt pulling force on the tube. Should axial displacement of a tube occur and go unnoticed, further fluids supplied through the tube may place the patient at risk. On the other hand, if the clamping jaws are closed tightly about a soft feeding tube to avoid any possibilities of displacement, the lumen of the tube, depending in part on the size of the tube involved, may become objectionably constricted.

Accordingly, the present invention is concerned with a nasogastric tube holding device that has many of the important advantages of the device disclosed in the aforementioned copending application but is particularly useful with relatively soft nasogastric feeding tubes over a wide range of sizes. Clamping forces may be easily applied to retain feeding tubes as small as 3 French (1 millimeter) or as large as 18 French (6 millimeters) and, even if excessive clamping forces should happen to be applied, lumen occlusion is a practical impossibility. Because of its distinctive multi-plate jaw construction and the beveled edges provided by such plates, the jaw assembly securely holds even a relatively soft feeding tube against slipping movement without the application of extraordinary clamping force.

In addition, the nasogastric tube holding device of this invention is adjustable and releasable with its jaw-latching mechanism exposed above the pivot pin for ready access when adjustment or release of the jaws is desired. Despite such accessibility, the latching mechanism does not project any appreciable distance above the pin so as to obstruct or interfere with the wearer's vision. Further, the latching mechanism is constructed so that, despite its accessibility, release takes place only if certain specific manipulative actions are performed, thereby insuring against inadvertent or unintentional release.

Briefly, the assembly of this invention takes the form of a flexible nose pad adapted for adhesive attachment over a wearer's nose, a mounting pin secured to the pad with its axis generally parallel with the pad and with an end portion projecting from the pad's distal edge, a pair of opposing clamping jaws pivotally supported by the projecting end portion of the pin for movement between open position and a plurality of closed positions, and releasable latching means disposed above the pin for selectively latching the jaws in any of their closed positions. Each of the jaws has a plurality of spaced, parallel clamping plates disposed beneath the pin for clamping and holding a nasogastric tube, particularly a feeding tube, when the jaws are closed. A characteristic of the jaws is that they are engagable with a nasogastric tube from four directions with the lines of contact generally defining a quadrangle of approximately diamond shape, making it impossible as a practical matter to apply clamping forces to even a relatively soft feeding tube that are of sufficient magnitude to occlude the lumen of that tube.

The clamping plates of one jaw are offset in relation to the clamping plates of the other jaw for interdigitation of the plates when the jaws are closed. Therefore, the lines of contact not only extend on four sides of the tube when the tube is viewed in cross section but are also applied at several axially-spaced zones when the tube is viewed in longitudinal section. At least some, and preferably all, of the clamping plates provide beveled contact surfaces terminating in narrow tube-contacting edges that effectively grip the outer surface of a tube for securing that tube against slippage.

The releasable latching means includes two parallel series of ratchet teeth provided by one of the clamping jaws and two flexible latching arms provided by the other jaw. The arms have end portions with latching teeth for engagement with the ratchet teeth for securely holding the clamping jaws in any selected position of adjustment. Since the ratchet teeth of the two series are offset relative to each other, and since the latching teeth of the flexible arms are disposed in side-by-side alignment with each other, only the latching teeth of one of the arms makes latching engagement with the ratchet teeth at any given time. The result is an arrangement which permits close or fine adjustment of the latching mechanism over the full range of tube sizes capable of being clamped by the mechanism.

Other features, advantages, and objects of the invention will become apparent from the specification and drawings.

DRAWINGS

DETAILED DESCRIPTION OF PREFERRED EMBODIMENT

Figure 1:
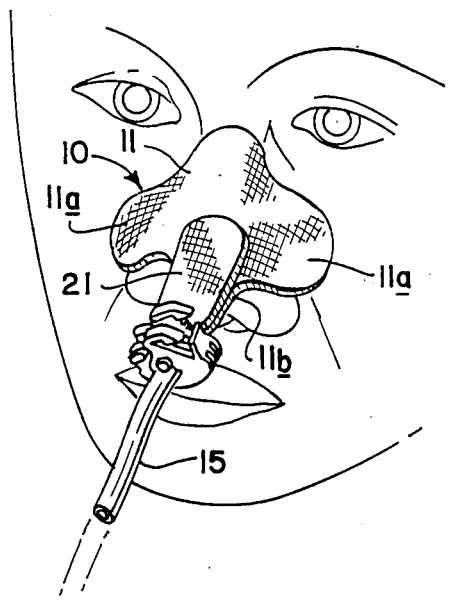
FIG. 1 is a perspective view showing a device of the present invention as it would appear when worn by a patient.

Referring to the drawings, the numeral 10 generally designates a nasogastric tube holder including a flexible adhesive pad 11 and a pair of pivotally-mounted clamping jaws 12 and 13. The jaws are pivotally supported by a mounting pin 14 that is generally coplanar with the adhesive pad and that, as shown most clearly in FIGS. 1 and 2, has a head end portion 14a that protrudes from one edge of the pad.

Figure 2:
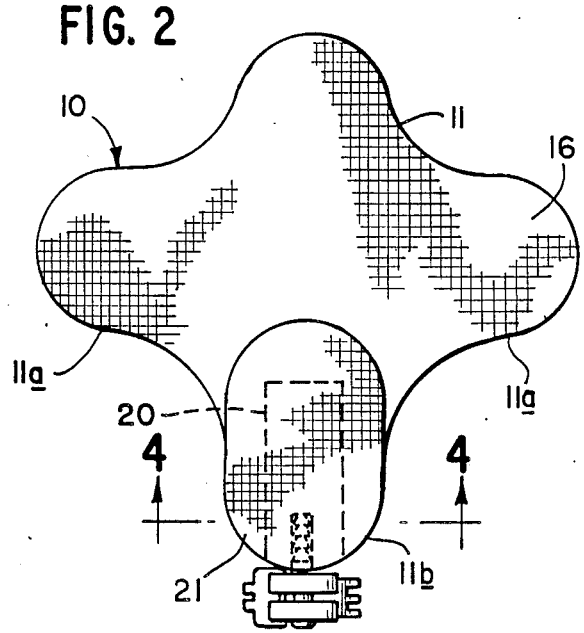
FIG. 2 is a top plan view of the device.

The pad includes a pair of wing portions 11a that are dimensioned and arranged to extend downwardly and outwardly along opposite sides of a wearer's nose and a central portion 11b that extends along the ridge of the nose adjacent to the tip thereof (FIG. 1). While some protrusion of the central portion 11b beyond the tip of the nose is acceptable, such protrusion should be kept to a minimum to avoid the possibility of pistoning action should longitudinal forces be exerted on nasogastric tube 15.

The pad preferably includes a thin layer 16 of soft, flexible, porous sheet material. A particularly effective material is believed to be the non-woven, non-occlusive sheet material formed of spunlaced polyester marketed by Minnesota Mining & Manufacturing Co. under the designation 3M Tape No. 1776 or by Fasson Tape under the designation MED 5322P. It is to be understood, however, that other materials having similar properties may also be used. Any soft, pliant fabric, whether woven or unwoven, that is sufficiently porous to allow for the passage of water vapor and gases therethrough, may be effectively used.

Along the underside of layer 16 is a layer or coating 17 of pressure sensitive adhesive which may be a typical medical-grade acrylic adhesive as commonly used in the manufacture of adhesive tapes for medical use. If desired, a cushioning layer of a soft, tacky, and deformable skin barrier material may be provided along the underside of central portion 11b.

An insert plate 20 is disposed above layer 16 and is held in place by a patch 21 having an adhesive coating along its undersurface. The patch 21 may be formed of the same porous material as layer 16 and its adhesive coating may be of the same adhesive material that coats the underside of layer 16.

The insert plate 20 is generally rectangular in outline and arcuate in section, with the concave undersurface 20a of the plate facing downwardly and engaging the upper surface of porous layer 16. Because of its cross sectional curvature, the insert plate readily adapts to the curvature along the ridge of a wearer's nose. In addition, the curvature of the flexible plate tends to impose a curvature in the pad itself. The upper patch 21 extends over the insert plate and conceals the plate except for the front face 20b that terminates immediately adjacent the front edge of central portion 11b of the pad. The front portion of the insert plate includes an enlargement 23 in which a forwardly facing socket or opening 24 is formed. That socket receives and retains the barbed end 14b of mounting pin 14 when the parts are fully assembled.

The flexible nose pad so far described is substantially the same in construction and operation as the pad disclosed in the aforementioned copending co-owned application 197,826, filed May 23, 1988. Reference may be had to such application for further details of construction of the pad.

Clamping jaws 12 and 13 have apertured hub portions 25 and 26, respectively, that pivotally receive the shank of mounting pin 14. The enlarged head 14c at the end of protruding portion 14a retains the jaws upon the pin and in close proximity to the end of insert plate 20. The pivotally mounted jaws may be swung between fully open positions as shown in FIG. 5 and any of a multiplicity of closed positions, one of which being illustrated in FIG. 6.

Figure 3:
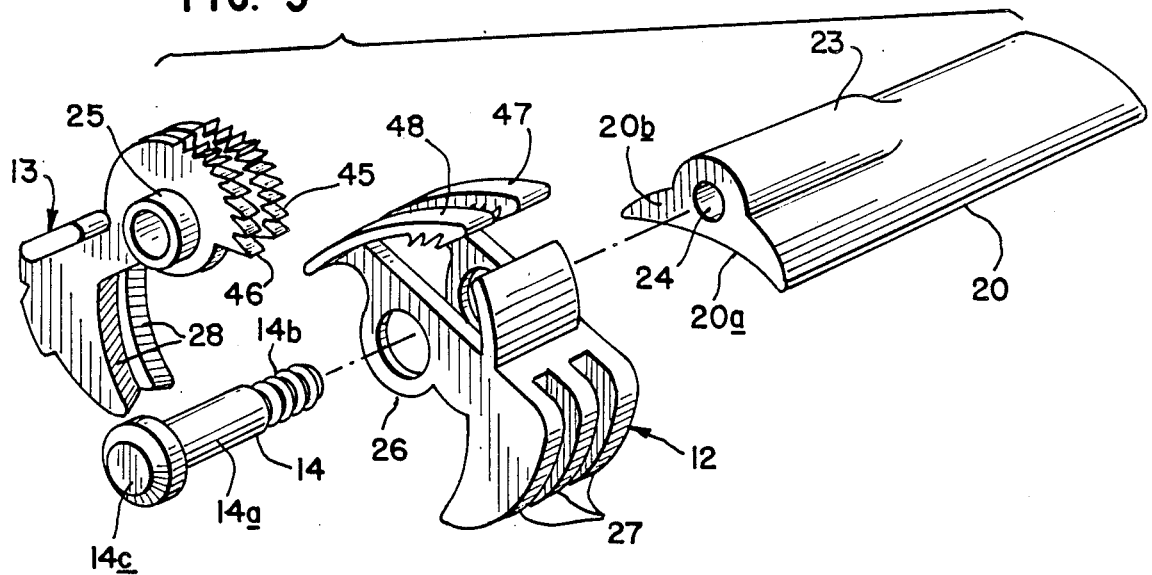
FIG. 3 is an enlarged exploded perspective view showing major elements of the assembly.
Figure 4:
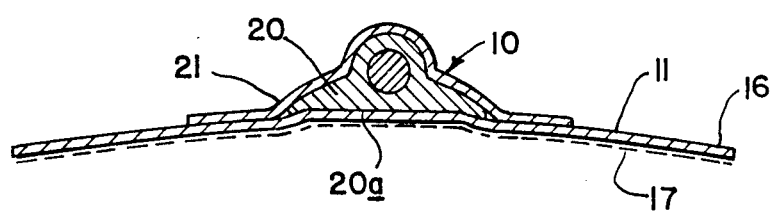
FIG. 4 is an enlarged cross sectional view taken along line 4—4 of FIG. 2.

Each of the jaws has a plurality of spaced parallel clamping plates disposed beneath the mounting pin 14 for clamping a nasogastric tube 15 therebetween when the jaws are closed. As shown most clearly in FIG. 3, jaw 12 includes three such clamping plates 27 while jaw 13 has two such plates 28, with the clamping plates of one jaw being offset in relation to the clamping plates of the other jaw for interdigitation when the jaws are closed.

Figure 5:
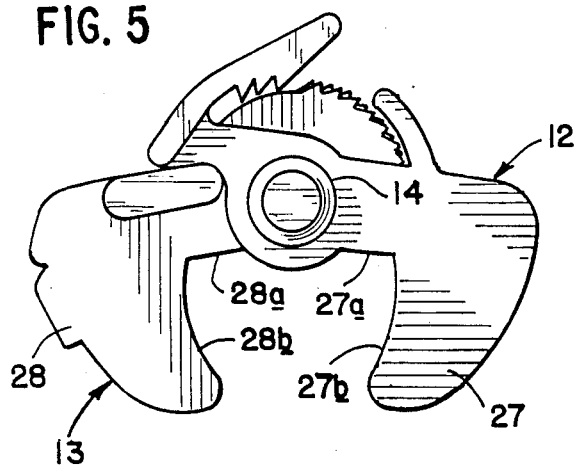
FIG. 5 is an enlarged end view of the clamping and latching assembly of the invention, showing the clamping jaws in open positions.
Figure 6:
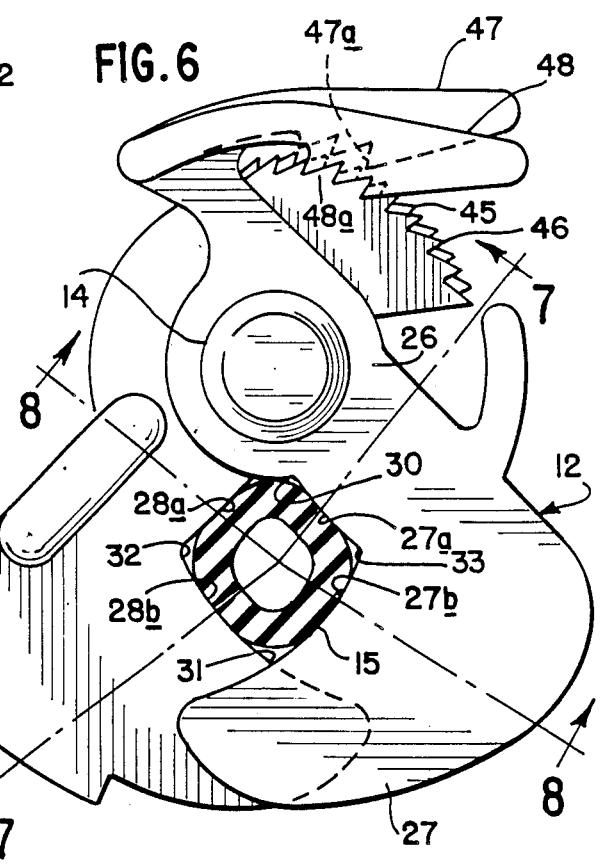
FIG. 6 is a greatly enlarged elevational view similar to FIG. 5 but showing the jaws in closed positions for holding a nasogastric tube in place.

Referring to FIGS. 5 and 6, it will be observed that each clamping plate 27 of jaw 12 has a pair of inner edge portions 27a and 27b extending generally at right angles to each other. Similarly, each plate 28 of jaw 13 has a pair of inner edge portions 28a and 28b disposed generally at right angles to each other. When the jaws are closed, such edge portions of the respective jaws approach each other to define a quadrangle of generally diamond shape. Two corners of the quadrangle, designated in FIG. 6 by numerals 30 and 31, are located in a generally vertical plane that extends through the longitudinal axis of mounting pin 14 whereas the other two corners 32, 33 oppose each other generally along the directions of movement of the clamping jaws. The result is a jaw construction which exerts clamping forces against a nasogastric tube 15 along four major lines of contact, forcing the tube into a generally diamond-shaped cross sectional configuration and, because of the orientation of the diamond (with two of its corners 32, 33 being formed by each of the respective jaws and two other corners 30, 31 each being formed by the interfit between the pair of such jaws), even the application of excessive force to a relatively soft feeding tube will not result in complete occlusion of the lumen of that tube.

Figure 7:
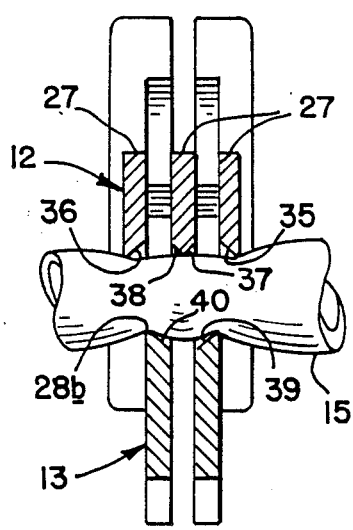
FIG. 7 is a sectional view, on a scale smaller than that of FIG. 6, taken along line 7—7 of FIG. 6.
Figure 8:
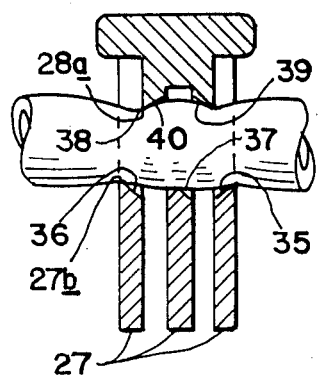
FIG. 8 is a sectional view to the same scale as FIG. 7 taken along line 8—8 of FIG. 6.

FIGS. 7 and 8 reveal that when the clamping jaws are viewed in longitudinal section, the inner edge portions 27a, 27b, 28a, and 28b are beveled. Of the three clamping plates 27 provided by jaw 12, the outboard plates have single beveled surfaces 35 and 36, respectively, and the central plate has double beveled surfaces 37 and 38. It will be observed that the beveled surfaces terminate in the narrow tube-contacting edges 27a, 27b and that the beveled surfaces of adjacent clamping plates of the same jaw slope inwardly away from each other. Thus, beveled surfaces 35 and 37 slope away from each other as they progress inwardly in the direction of nasogastric tube 15, and the same observation is applicable to the beveled surfaces 36 and 38.

The paired clamping plates 28 similarly have beveled surfaces 39, 40 terminating in narrow tube-contacting edges 28a and 28b. Again, the beveled surfaces 39, 40 of the faced clamping plates 28 slope away from each other in an inward direction towards nasogastric tube 15. The result is a construction in which the narrow tube-contacting edges of the interfitting clamping plates 27, 28 engage the outer surface of a nasogastric tube along lines of contact that are spaced apart along the full axial dimension of the interdigitating clamping plate assembly. The narrow lines of contact with a nasogastric tube, the axial spacing between those lines, and the multiplicity of such lines, all contribute in providing a secure non-sliding grip between the jaw assembly and a nasogastric tube. The gripping action is further promoted by the fact that the contact edges form a generally square or diamond pattern when viewed in cross section (FIG. 6), thereby altering the cross sectional configuration of a tube in the axial zone of contact by the clamping jaws. While the jaws, taken together, provide a total of five interdigitating clamping plates, it is to be understood that even a greater number, or perhaps in some cases a smaller number, might be provided.

Figure 9:
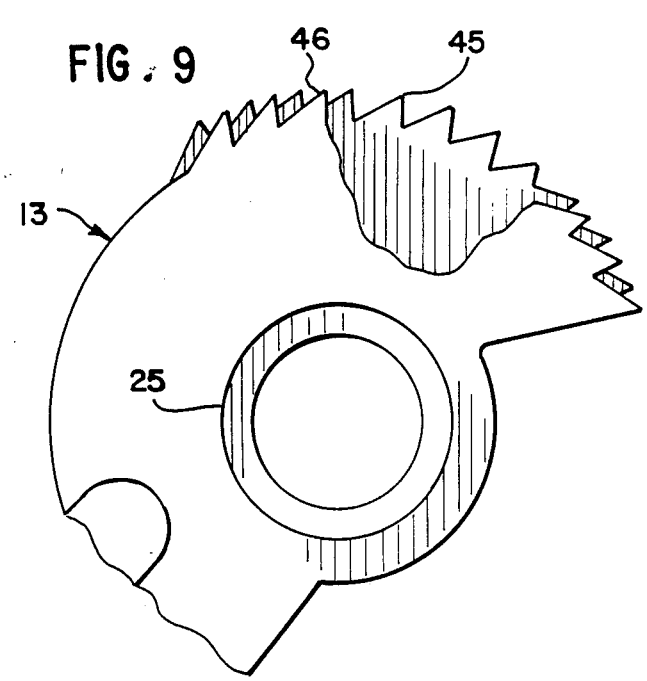
FIG. 9 is a fragmentary view of that portion of one of the jaws providing two series of ratchet teeth, with a portion of the jaw cut away to illustrate the offset relationship more clearly.

The releasable latching means takes the form of two arcuate series of ratchet teeth 45, 46 provided by one of the clamping jaws 13 and two flexible latching arms 47, 48 provided by the other clamping jaw 12. It will be observed that the ratchet teeth 45, 46 extend across the top of hub portion 25 and, when the device is in use, are generally located above the axis of mounting pin 14. Each series of teeth follows an arc that is coaxial with pin 14 and the opening of hub portion 25; however, as depicted most clearly in FIG. 9, the teeth of the two series 45, 46 are staggered with each tooth of one series being offset so that its tip is at a midpoint between successive teeth of the adjacent series.

Latching arms 47, 48 are disposed above hub portions 25, 26, and above mounting pin 14, when the device is in operative position. The arms are provided with downwardly-facing latching teeth 47a and 48a respectively with each jaw preferably having a plurality of such teeth, three being shown in the embodiment illustrated. Unlike the ratchet teeth of series 45, 46, the teeth 47a and 48a of the respective latching arms are not offset but are disposed in side-by-side alignment. As a result, only one set of latching teeth 47 or 48 makes full latching engagement with ratchet teeth 45 or 46 at any given time. The relationship is depicted most clearly in FIG. 6 where it will be observed that the teeth 48a of arm 48 are fully engaged with the ratchet teeth of series 46 whereas arm 47 is flexed upwardly with its teeth 47a out of meshing engagement with the ratchet teeth of series 45. Such a construction provides a fine degree of latching adjustment (a total of 20 incremental latching positions are provided by an embodiment of the invention as illustrated) while at the same time insuring secure latching engagement because of the relatively large size of the teeth of the ratchet teeth and latching teeth and because a plurality of latching teeth are provided by each arm. Precise adjustment of the latching mechanism may therefore be achieved without the risk that sudden forces exerted upon a nasogastric tube might cause slipping or stripping of the teeth of the latching mechanism. Furthermore, because of the relatively large size of the teeth, and because two latching arms are provided, unlatching of the mechanism requires deliberate lifting of both latching arms into releasing positions. Therefore, despite the readily-accessible position of the latching mechanism, which greatly facilitates intentional adjustment or release of the mechanism, the tube holding mechanism offers exceptional security against unintentional release.

While in the foregoing I have disclosed an embodiment of the invention in considerable detail for purposes of illustration, it will be understood by those skilled in the art that many of these details may be varied without departing from the spirit and scope of the invention.

I claim:

1. A nasogastric tube holder, comprising a flexible nose pad having an upper surface and having an adhesive-bearing lower surface for adhesive attachment of the pad over the ridge of a wearer's nose; a mounting pin secured to said pad; said pin having its axis generally parallel with said pad and having an end portion projecting from an edge of said pad; and a pair of opposing clamping jaws pivotally supported by said projecting end portion of said pin for movement between an open position and a plurality of closed positions; said jaws having releasable latching means disposed above said pin for selectively latching said jaws in any of said closed positions; each of said jaws also having a plurality of spaced parallel clamping plates disposed beneath said pin for clamping a nasogastric tube therebetween when said jaws are closed; said clamping plates of one jaw being offset in relation to the clamping plates of the other jaw for interdigitation therewith when said jaws are closed.

2. The holder of claim 1 in which said clamping plates have beveled inner surfaces terminating in narrow tube-contacting inner edges.

3. The holder of claim 2 in which said beveled surfaces of adjacent clamping plates of the same jaw slope inwardly away from each other.

4. The holder of claims 2 or 3 in which said narrow tube-contacting inner edges of each jaw includes a pair of edge portions disposed generally at right angles to each other; said pairs of edge portions of both jaws together defining a tube-receiving opening of generally diamond-shaped configuration when said jaws are closed.

5. The holder of claim 1 in which said jaws have unequal numbers of said clamping plates.

6. The holder of claim 5 in which one of said jaws has three of said clamping plates and the other of said jaws has two of said clamping plates.

7. The holder of claims 1 or 2 in which said releasable latching means includes two arcuate series of ratchet teeth provided by one of said clamping jaws and two flexible latching arms provided by the other of said jaws; said latching arms having end portions with latching teeth for engagement with said ratchet teeth for holding said clamping jaws in selected closed positions.

8. The holder of claim 7 in which said ratchet teeth of one of said series are offset relative to the ratchet teeth of the other of said series.

9. The holder of claim 8 in which said latching teeth of said flexible arms are disposed in side-by-side alignment with each other so that the latching teeth of only one of said arms is in latching engagement with the ratchet teeth of one of said series at any given time.

10. The holder of claim 7 in which each of said arms includes a plurality of said latching teeth.

* * * * *